US009782069B2

(12) United States Patent
Bellamy et al.

(10) Patent No.: US 9,782,069 B2
(45) Date of Patent: Oct. 10, 2017

(54) CORRECTING SYSTEMATIC CALIBRATION ERRORS IN EYE TRACKING DATA

(71) Applicant: International Business Machines Corporation, Armonk, NY (US)

(72) Inventors: Rachel K. E. Bellamy, Bedford, NY (US); Bonnie E. John, New York, NY (US); John T. Richards, Honeoye Falls, NY (US); Calvin B. Swart, Poughkeepsie, NY (US); John C. Thomas, Jr., Solana Beach, CA (US); Sharon M. Trewin, Croton-on-Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 518 days.

(21) Appl. No.: 14/534,348

(22) Filed: Nov. 6, 2014

(65) Prior Publication Data
US 2016/0128568 A1    May 12, 2016

(51) Int. Cl.
*A61B 3/113* (2006.01)
*A61B 3/00* (2006.01)
*A61B 3/032* (2006.01)
*A61B 5/16* (2006.01)

(52) U.S. Cl.
CPC .............. *A61B 3/113* (2013.01); *A61B 3/005* (2013.01); *A61B 3/0025* (2013.01); *A61B 3/0083* (2013.01); *A61B 3/0091* (2013.01); *A61B 3/032* (2013.01); *A61B 5/168* (2013.01)

(58) Field of Classification Search
CPC ....... A61B 3/113; A61B 3/0025; A61B 5/168; A61B 3/0083; A61B 3/032; A61B 3/005

USPC .......... 702/94, 558, 559; 351/210, 205, 246, 351/209; 382/103; 348/78; 375/346, 375/349; 345/8
See application file for complete search history.

(56) References Cited

U.S. PATENT DOCUMENTS

| 4,582,403 A | 4/1986 | Weinblatt |
| 5,657,356 A | 8/1997 | Ozaki |

(Continued)

FOREIGN PATENT DOCUMENTS

| EP | 1578290 B1 | 3/2012 |
| WO | 2010141403 A1 | 12/2010 |
| WO | 2011127609 A1 | 10/2011 |

OTHER PUBLICATIONS

A.J. Hornof et al., "Cleaning Up Systematic Error in Eye-Tracking Data by Using Required Fixation Locations," Behavior Research Methods, Instruments, & Computers, Nov. 2002, pp. 592-604, vol. 34, No. 4.

(Continued)

*Primary Examiner* — Carol S Tsai
(74) *Attorney, Agent, or Firm* — Alexa L. Ashworth; Ryan, Mason & Lewis, LLP

(57) ABSTRACT

Systems and methods are provided for post-hoc correction of calibration errors in eye tracking data, which take into consideration calibration errors that result from changes in user position during a user session in which the user's fixations on a display screen are captured and recorded by an eye tracking system, and which take into consideration errors that occur when the user looks away from a displayed target item before selecting the target item.

20 Claims, 10 Drawing Sheets

(56) References Cited

U.S. PATENT DOCUMENTS

| | | | | |
|---|---|---|---|---|
| 6,027,216 | A * | 2/2000 | Guyton | A61B 3/113 351/200 |
| 6,601,021 | B2 * | 7/2003 | Card | G06F 3/013 340/3.6 |
| 6,634,749 | B1 | 10/2003 | Morrison et al. | |
| 7,460,940 | B2 * | 12/2008 | Larsson | A61B 3/113 180/272 |
| 7,657,062 | B2 | 2/2010 | Pilu | |
| 7,676,063 | B2 * | 3/2010 | Cohen | H04N 7/148 382/100 |
| 7,736,000 | B2 | 6/2010 | Enriquez et al. | |
| 7,916,897 | B2 * | 3/2011 | Corcoran | G06K 9/00228 382/103 |
| 8,717,393 | B2 * | 5/2014 | Pasquero | G06F 3/013 345/211 |
| 9,265,416 | B2 * | 2/2016 | Klin | A61B 3/113 |
| 9,442,565 | B2 * | 9/2016 | Lohrenz | G06F 3/013 |
| 9,477,317 | B1 * | 10/2016 | Clements | G06F 3/017 |
| 9,480,397 | B2 * | 11/2016 | Larsen | G06K 9/00604 |
| 9,558,714 | B2 * | 1/2017 | Pasquero | G06F 3/013 |
| 9,596,508 | B2 * | 3/2017 | McCoy | G06K 9/00597 |
| 9,629,543 | B2 * | 4/2017 | Agichtein | A61B 3/113 |
| 2004/0179716 | A1 * | 9/2004 | Tafuku | G06K 9/00604 382/103 |
| 2010/0208205 | A1 * | 8/2010 | Tseng | A61B 3/113 351/209 |
| 2012/0230553 | A1 * | 9/2012 | Bijalwan | G06K 9/00604 382/117 |
| 2013/0050268 | A1 * | 2/2013 | Lohrenz | G06F 3/013 345/660 |
| 2013/0090562 | A1 * | 4/2013 | Ryan | A61B 3/032 600/473 |
| 2014/0253876 | A1 * | 9/2014 | Klin | A61B 3/113 351/210 |
| 2014/0282646 | A1 * | 9/2014 | McCoy | G06K 9/00597 725/12 |
| 2014/0313129 | A1 * | 10/2014 | Elvesj | G06F 1/3287 345/156 |
| 2015/0085251 | A1 * | 3/2015 | Larsen | G06K 9/00604 351/206 |
| 2016/0262612 | A1 * | 9/2016 | Klin | A61B 3/113 |

OTHER PUBLICATIONS

K.P. White, Jr. et al., "Spatially Dynamic Calibration of an Eye-Tracking System," IEEE Transactions on Systems, Man and Cybernetics, Jul./Aug. 1993, pp. 1162-1168, vol. 23, No. 4.

J.E. Hoffman et al., "The Role of Visual Attention in Saccadic Eye Movements," Perception & Psychophysics, Aug. 1995, pp. 787-795, vol. 57, No. 6.

C. Andrá et al., "How Students Read Mathematical Representations: An Eye Tracking Study," Proceedings of the 33rd Conference of the International Group for the Psychology of Mathematics Education, Jan. 2009, 8 pages, vol. 1, Thessaloniki, Greece.

C. Conati et al., "Eye-Tracking for User Modeling in Exploratory Learning Environments: an Empirical Evaluation," Journal Knowledge-Based Systems, Knowledge-Based Systems, Aug. 2007, pp. 557-574, vol. 20, No. 6.

Y. Zhang et al., "Mode-of-Disparities Error Correction of Eye-Tracking Data," Behavior Research Methods, Sep. 2011, pp. 834-842, vol. 43, No. 3.

* cited by examiner

500

600

700

800

900

CORRECTING SYSTEMATIC CALIBRATION ERRORS IN EYE TRACKING DATA

TECHNICAL FIELD

The field generally relates to data processing and, in particular, to systems and methods for correcting systematic calibration errors in eye tracking data.

BACKGROUND

In general, eye tracking systems are utilized in various applications to detect an individual's visual fixation (or gaze point) on a display screen and/or track the individual's eye motion relative to the individual's head. An individual's eye movement includes fixations and saccades. The term "fixation" refers to the maintaining of the visual gaze on a single location, i.e., when eye gaze pauses in a certain position. By way of example, a fixation can have a duration in a range of about 100 ms (when reading text) to about 350 ms when viewing a scene. The term "saccades" refers to quick, simultaneous movements of both eyes in the same direction.

An eye tracking system is typically implemented using an optical-based eye tracking device to detect fixations and measure eye movement. In a typical optical-based eye tracking system, infrared light is emitted towards a user's face, and the infrared light reflected from the user's eyes is captured by a video camera or some other application specific optical sensor. Depending on the application, some video-based eye tracking devices are configured to capture features such as corneal reflection and the center of the pupil, while other eye tracking systems are configured to capture double reflections from the front and back of the retina, for example. The captured information is then analyzed to determine eye movement and gaze direction based on changes in reflections.

Optical-based eye tracking systems are used to estimate gaze direction in various research studies such as cognitive linguistics and product design, for example, in which tracking a user's gaze location on a computer screen provides useful information. For example, gaze tracking is implemented in usability studies for computer user interfaces, wherein web designers and other application designers are interested to know what displayed features of a web page or user interface are viewed (or not viewed) by users, and to understand how users perform complex computer tasks or otherwise interact with an application user interface.

It is understood that eye tracking systems do not actually determine an absolute gaze direction or fixation location on a display screen, and can only measure changes in gaze direction. To accurately estimate a user's gaze direction or fixation location on a display screen, eye tracking systems implement a calibration process to provide an accurate mapping from eye position to display location. In general, a calibration procedure involves displaying a series of calibration items at different locations across a computer display, and recording data values that correspond to each gaze position of the user as the user looks at each displayed calibration item. While a set of calibration data can be effective to process eye tracking data and determine gaze points of a user on a display screen, systematic calibration errors are introduced into recorded gaze point locations for eye tracking data when the user changes his or her head position relative to the display after calibration is completed, which can render the captured data unusable.

SUMMARY

In general, embodiments of the invention include systems and methods for correcting systematic calibration errors in eye tracking data. For example, in one embodiment of the invention, a method is provided for correcting systematic calibration error in eye tracking data acquired using an eye tracking system, wherein the method includes accessing recorded information that is associated with a given session in which a user performs a computer task while selecting known target items that are displayed on a display screen during the session and while using the eye tracking system to record locations of user fixations on the display screen as the user views the display screen during the session. The recorded information includes (i) fixation data that include start time, display screen location, and duration information for each of a plurality of fixations recorded during the session, (ii) selection event data that include start time and display screen location information for each of a plurality of user selection events recorded during the session; and (iii) known target location data that include display screen location information for each of a plurality of known target items that are displayed during the session. The method further includes processing the obtained information to identify a known target item selected by the user, and processing the obtained information to identify a recorded fixation, if any, which most likely corresponds to the identified known target item selected by the user, wherein a recorded fixation which was not active at a time that the identified known target item was selected by the user, is considered as a candidate fixation. A distance vector is computed between the identified recorded fixation and the corresponding identified known target item, and the computed distance vector is stored as calibration error information for the identified recorded fixation and the corresponding identified known target item.

In another embodiment of the invention, a fixation that is deemed most likely to correspond to the identified known target item selected by the user is identified as the recorded fixation (i) which falls within a predefined time window prior to the time that the identified known target item was selected by the user, and (ii) which is nearest to a center region of the identified known target item selected by the user.

In yet another embodiment of the invention, a fixation that is deemed most likely to correspond to the identified known target item selected by the user is identified as the recorded fixation (i) which falls within a predefined time window prior to the time of selection of the identified known target item, (ii) which has a start time that is nearest in time to the time of selection of the identified known target item, but which start time is prior to the time of selection of the identified known target item by a predetermined amount of time, and (iii) which has a duration that meets a minimum predefined duration value.

In another embodiment of the invention, a method is provided to compute calibration error information for fixations that do not correspond to any known target item selected by the user. The method includes computing a calibration error vector for the identified fixation by taking a weighted average of distance measures of a set of target fixations that are nearest in both space and time to the identified fixation.

These and other embodiments of the invention will be described or become apparent from the following detailed description of embodiments, which is to be read in conjunction with the accompanying drawings.

DETAILED DESCRIPTION

Figure 1:
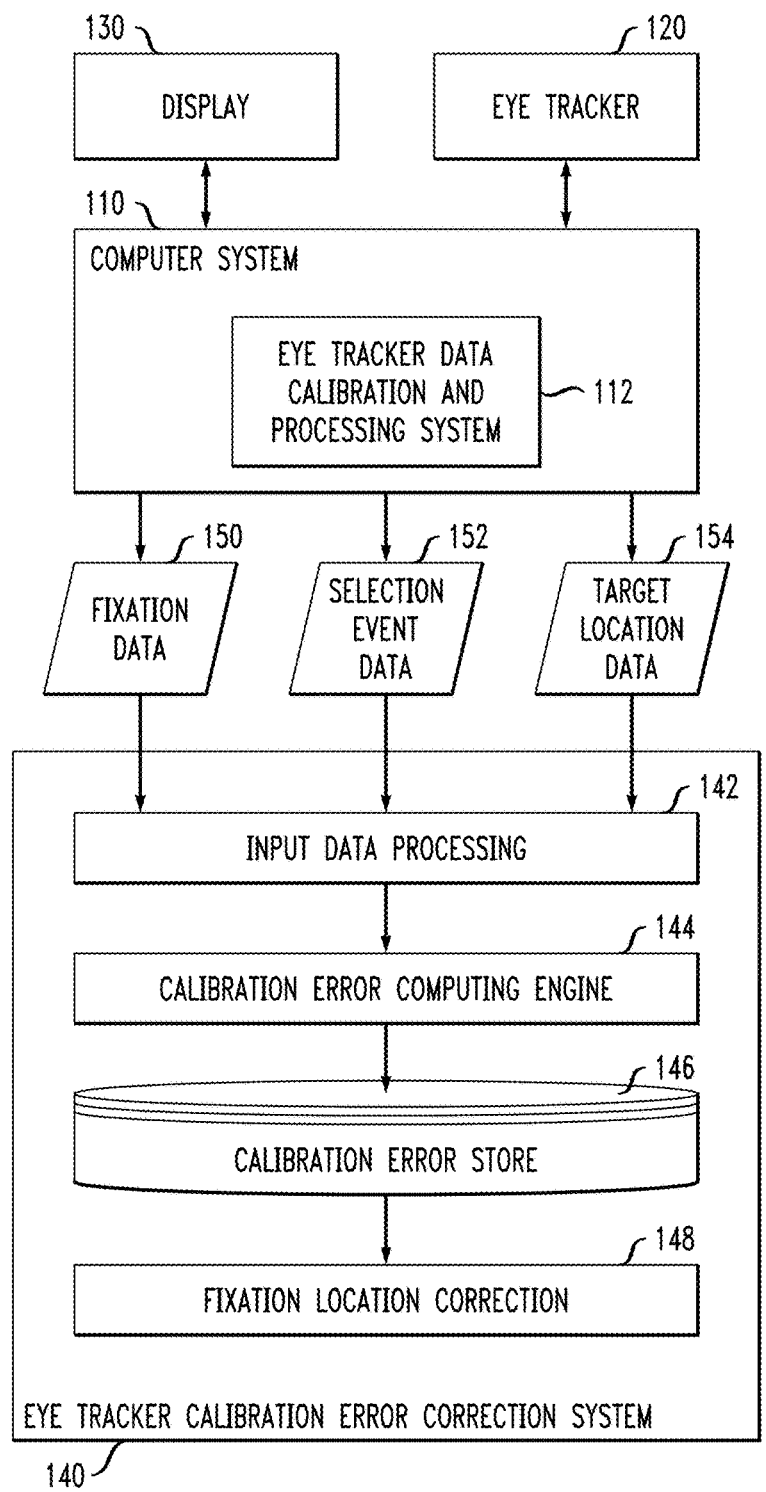
FIG. 1 is a block diagram of a system for capturing and processing eye tracking data, according to an embodiment of the invention.

FIG. 1 is a block diagram of a system 100 for capturing and processing eye tracking data according to an embodiment of the invention. In general, the system 100 comprises a computer system 110 having an eye tracker data calibration and processing system 112. The computer system 110 is coupled to an eye tracker device 120 and a display device 130. The system 100 further comprises an eye tracker calibration error correction system 140 which includes an input data processing module 142, a calibration error computing engine 144, a calibration error data store 146, and a fixation location correction module 148.

Collectively, the eye tracker device 120 and eye tracker data calibration and processing system 122 implement an eye tracking system that is configured to detect an individual's visual fixation (or gaze point) on a display screen of the display device 130. The display device 130 can be a separate computer monitor or a laptop computer screen, for example. In one embodiment of the invention, the eye tracker device 120 is an optical-based device comprising one or more near-infrared (IR) light projectors and optical sensors, with some image processing functions, wherein the eye tracker device 120 can be mounted to a bottom of the display device 130 or otherwise be incorporated as part of the display device 130. By way of specific example, in one embodiment of the invention, the eye tracker device 120 comprises at least one near-IR LED (light emitting diode) and a camera device, wherein the near-IR LED is coaxially disposed along an optical centerline of a lens of the camera, wherein the LED emits a beam of IR light that illuminates a user's face. The camera device (or other optical sensor array) of the eye tracker device 120 is configured to detect and capture the near-IR light that is reflected from one or both of the user's eyes, and send the captured eye tracker data to the eye tracker data calibration and processing system 112.

The eye tracker data calibration and processing system 112 is configured to process eye tracking data received from the eye tracker device 120 to perform various operations. For example, the eye tracker data calibration and processing system 112 is configured to perform a calibration operation. In general, a calibration operation is initially performed to establish a set of calibration parameters for a given individual. The set of calibration parameters for the given individual is utilized by the eye tracker data calibration and processing system 112 during real-time operation to effectively map image pixel coordinates of the display device 120 to an approximate gaze point location of the individual using vector transformation techniques that are well-known to those of ordinary skill in the art.

For example, a calibration process for an individual can be implemented as follows. The individual will sit in front of the display device 130 and maintain his or her head as stationary as possible during the calibration process. During the calibration process, a set of known targets (with known pixel coordinates) are displayed on the screen at different locations. While the individual gazes at a given known target on the display device 130, the user will "select" the known target by, e.g., placing a mouse cursor on the known target and clicking the mouse button. For a given selection event (e.g., mouse click), the individual's gaze point location on the display screen is determined for the given selection event (via vector analysis techniques) based on infrared light which is reflected from the individual's eyes and captured by the eye tracker device 120 at the time the individual selects the displayed target. This process is repeated for each of the known targets that are displayed during the calibration process to generate a set of calibration parameters for the given individual. As noted above, the set of calibration parameters is then used during real-time operation to map eye position to display location as the individual interacts with a given computer application or task.

While the eye tracking system implements a calibration process to provide an accurate mapping from eye position to display location, if the individual changes his/her position relative to the display device 130 after calibration is completed, systematic calibration errors are introduced into the eye tracking data, and can render the data unusable. In this regard, the eye tracking calibration error correction system 140 is configured to correct systematic calibration errors in eye gaze data. In particular, the eye tracking calibration error correction system 140 is configured for post-hoc correction of calibration errors introduced by changes in head position of an individual, and to achieve this even when the captured eye tracking data has the individual looking away from a given displayed target before actually selecting the displayed target.

The eye tracking calibration error correction system 140 receives various data files from the eye tracker data calibration and processing system 112 including a fixation data file 150, a selection event data file 152, and a target location data file 154. The data files 150, 152 and 154 comprise information regarding eye tracking data that is captured for a given individual during a given real-time session in which the individual performs some computer task or interacts with a given application on the computer system 110, for example. In particular, in one embodiment of the invention, the fixation data 150 and selection event data 152 collectively provide information regarding the time and location of detected gaze points (eye fixations) and user selection events (e.g., mouse clicks) on the display screen of the display device 130, which is captured during a user session. In addition, the target location data 154 include location information regarding known targets that are displayed on the display device 130 during the user session in which the eye tracking data is collected by the eye tracker device 120.

In general, the input data processing module 142 receives and processes the input data files 150, 152 and 154 to identify and extract information which is used by the calibration error computing engine 144 to compute calibration error data that is stored in the calibration error data store 146. For example, in one embodiment of the invention, the input data processing module 142 implements functions that will be described below with reference to blocks 200, 202, 204, 210, 212, 214, 216, and 222 of FIG. 2, for example. Furthermore, in one embodiment of the invention, the calibration error computing engine 144 implements functions that will be described below with reference to blocks 206, 208, 218 and 220 of FIG. 2, for example.

In addition, the fixation location correction module 148 is configured to correct the location of fixations included in the fixation data file 150 using the calibration error data stored in the calibration error data store 146. For example, in one embodiment of the invention, the fixation location correction module 148 implements functions described in further detail below with reference to block 224 of FIG. 2, for example. In one embodiment of the invention, the eye tracker calibration error correction system 140 is implemented on a computing platform, computing device, server, etc., which is separate from the computer system 110 that is used to implement the eye tracking system (e.g., components 112 and 120). In another embodiment of the invention, the eye tracker calibration error correction system 140 is implemented on the same computer system 100 that is used to implement the eye tracking system, wherein the various modules/components of the eye tracker calibration error correction system 140 can be integrated with the eye tracker data calibration and processing system 112, for example.

Figure 2:
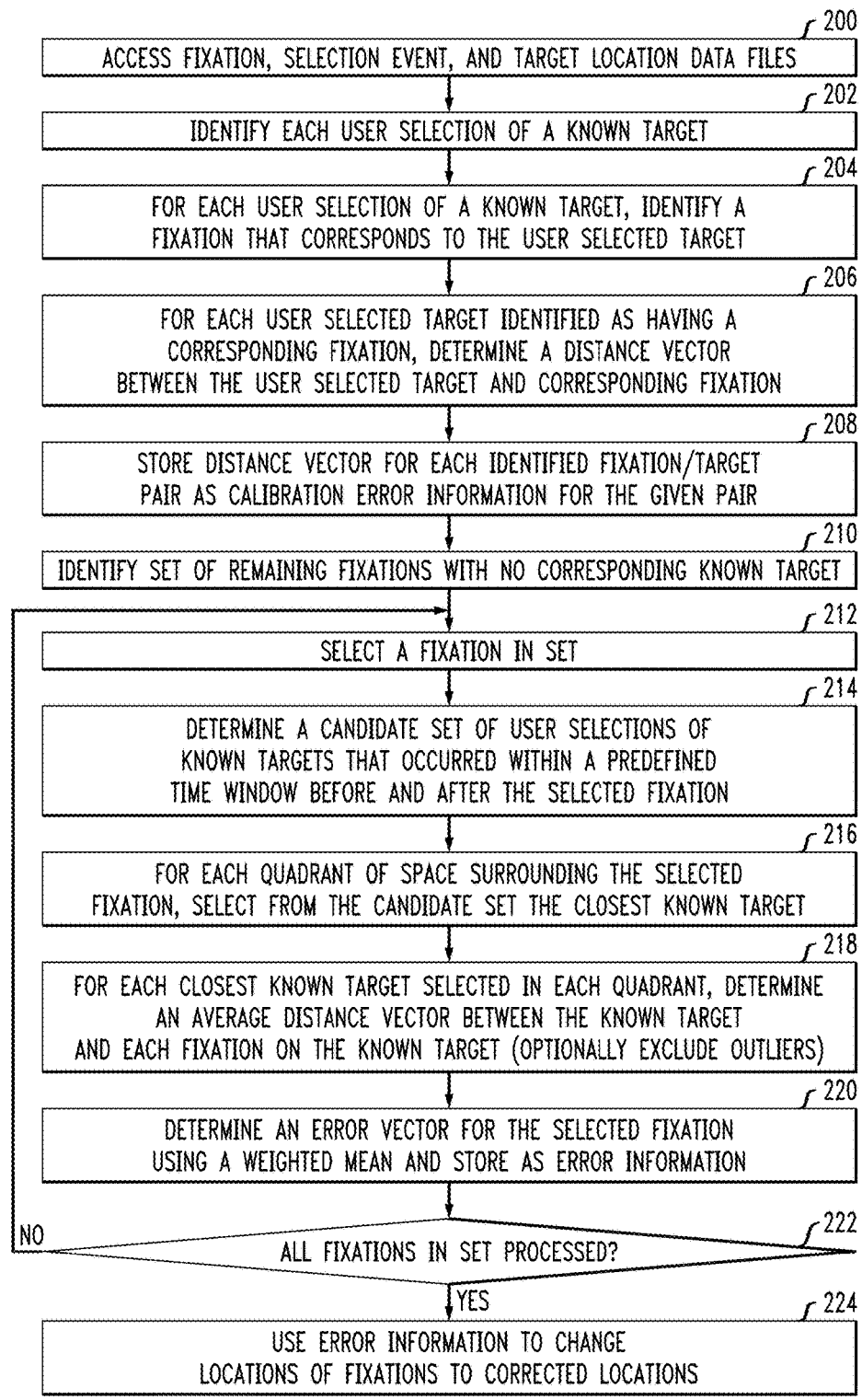
FIG. 2 is a flow diagram of a method for correcting systematic calibration errors in eye tracking data, according to an embodiment of the invention.

FIG. 2 is a flow diagram of a method for correcting systematic calibration errors in eye tracking data according to an embodiment of the invention. For illustrative purposes, the method of FIG. 2 will be discussed with reference to the system 100 of FIG. 1, wherein the method of FIG. 2 illustrates a mode of operation of the eye tracker calibration error correction system 140, according to an embodiment of the invention. An initial step is to obtain various data files, including a fixation data file, a selection event data file, and a target location data file, for a given user session (block 200). For example, as noted above, the eye tracker calibration error correction system 140 obtains a fixation data file 150, a selection event data file 152, and a target location data file 154 from the eye tracker data calibration and processing system 112. The data files 150, 152 and 154 comprise information regarding eye tracking data that is captured for a given individual during a given real-time session in which the individual performs some computer task or interacts with a given application.

In particular, in one embodiment of the invention, the following TABLE 1 illustrates an exemplary data structure for maintaining fixation data:

TABLE 1

| Timestamp | Fixation Index | Fixation Location [x, y] | Duration |
|---|---|---|---|
| ... | ... | ... | ... |
| 385 | Fixation0 | [550, 125] | 110 |
| 505 | Fixation1 | [58, 501] | 95 |

TABLE 1-continued

| Timestamp | Fixation Index | Fixation Location [x, y] | Duration |
|---|---|---|---|
| 600 | Fixation2 | [100, 512] | 395 |
| 995 | Fixation3 | [723, 233] | 402 |
| ... | ... | ... | ... |

In one embodiment of the invention, the fixation data shown in TABLE 1 includes a recorded sequence of "fixation events," wherein each row corresponds to a given fixation event, and wherein each fixation event includes a "timestamp," a "fixation index," a "fixation location," and "duration" data. Each "timestamp" specifies the time (e.g., milliseconds (ms)) at which the corresponding fixation was captured during the user session, and provides an indication of the time sequence of fixations that are captured during the user session. The "fixation index" provides a label (e.g., Fixation0, Fixation1, Fixation2, Fixation3, etc.) for the corresponding fixation event. The "fixation location" specifies the x,y display coordinate of the estimated center location of the user' gaze point on the display screen for the given fixation event. The "duration" specifies the time (e.g., milliseconds) of the given fixation event.

By way of further example, the following TABLE 2 illustrates an exemplary data structure for maintaining user selection event data:

TABLE 2

| Timestamp | Selection Index | Selection Location [x, y] | Known Target |
|---|---|---|---|
| ... | ... | ... | ... |
| 1000 | Click1 | [25, 456] | TargetA |
| ... | ... | ... | ... |

In particular, in one embodiment of the invention, the selection event data shown in TABLE 2 includes a recorded sequence of "selection events," wherein each row corresponds to a given selection event. A selection event can be, for example, user selection of some displayed item using a pointing device (e.g. mouse), or touchscreen contact, etc. Each selection event includes a "timestamp", a "selection index," and a "selection location." In another embodiment, as shown in TABLE 2, the selection event data may optionally include an identifier of the selected "known target" which is associated with the selection event. Each "timestamp" specifies the time (e.g., milliseconds) at which the corresponding selection event was captured during the user session. The "selection index" provides a label (e.g., Click1, Click2, ... ) for the corresponding selection event. The "selection location" specifies the x,y display coordinate of the selection event. The "known target" provides a label that corresponds to the displayed item (e.g., menu item, hyperlink, etc.) which was determined, a priori, to be the user selected target and included in the selection event data file 152.

In addition, the target location data 154 include location information regarding known targets that are displayed during the user session in which the eye tracking data is collected. For example, in one embodiment of the invention, the following TABLE 3 illustrates an exemplary data structure for maintaining known target location data:

TABLE 3

| Known Target | Location [x, y] |
| --- | --- |
| TargetA | [43, 430] |
| TargetB | [250, 325] |
| ... | ... |

In particular, in one embodiment of the invention, the known target location data shown in TABLE 3 includes a listing of all known targets (target index, TargetA, TargetB, . . . ) displayed during the user session, and the associated "location" information for the known targets. In one embodiment of the invention, the location information specifies the x,y display coordinate of the center location of the known (displayed) target. In another embodiment, the known target location information may further include a range of x,y coordinates (boundary) of the display area that is occupied by a given known target, in addition to the center coordinate.

Referring back to FIG. 2, after the fixation data, selection event data, and target location data files are obtained, a next step includes using the obtained information to identify each user selection of a known target (block 202). More specifically, in one embodiment of the invention, each user selection of a known target can be determined using the user selection event data 152, such as depicted in TABLE 2. For example, as shown in TABLE 2 above, the user selection event "Click1" corresponds to the known (displayed) target "TargetA." In this embodiment, such information is determined, a priori, by the eye tracker data calibration and processing system 112 and included in the selection event data 152 that is provided to the eye tracker calibration error correction system 140.

In another embodiment of the invention, each user selection of a known target can be determined (in block 202) using the selection event data 152 and the target location data 154. For example, as noted above, in one embodiment of the invention, the selection event data 152 may not a priori include the identified "known target." In such instance, the target of a given user selection event can be determined by correlating a given "selection location" coordinate (as shown in TABLE 2) with the location information of known targets (as provided in the target location data file 54) to determine a known target that corresponds to the given selection location coordinate. By way of specific example, as noted above, for each known target that is displayed during a user session, the target location data file 154 can include a range of x,y coordinates (boundary) of the display area that is occupied by the known target. Then, for a given user selection event included in the selection event data file 152, the associated "selection location" coordinate (as shown in TABLE 2) can be compared against the range of x,y coordinates for each known target (included in the target location data file 154) to determine if the coordinate of the given "selection location" falls within the specified range of x,y coordinates of any known target. The known target having a range of x,y coordinates which includes the coordinate of the "selection location" is identified as the user selected known target associated with the given user selection event.

Next, for each user selection of a known target (i.e., each user selected target identified in block 202), a method is implemented to identify a fixation that corresponds to the user selected target (block 204). In general, this process involves identifying which "fixation event" in the recorded sequence of fixation events contained in the fixation data file 150 most likely corresponds to a given user selected target based on timing and/or location information. Typically, when performing a computer task, a user will gaze at a displayed target item and then select the target item. In some instances, the user's gaze will remain fixed on the displayed target item while the user selects the displayed target item. In these instances, the time of the user selection event (i.e., time of selecting the displayed target item) corresponds to the time that the fixation event was recorded while the user was actually looking at the displayed target item. In other instances, the user can manipulate a pointing device to place a cursor on a displayed target item to be selected, and then look away before actually selecting the target item. In these instances, the time of the user selection event (i.e., time of selecting the displayed target item) corresponds to the time that the fixation event was recorded while the user was actually looking away from the displayed target item. Furthermore, in other instances in which the display device comprises a touch screen that allows a user to select a displayed item with the touch of a finger, for example, the user's finger may occlude a displayed target being selected, which may cause the user to not be looking at the displayed target when selecting it. In this regard, depending on the behavior of the user and/or the way in which displayed items are selected, it may be problematic to determine which fixation is actually associated with a user selected target.

This issue is illustrated using the data shown in TABLES 1 and 2, for example. As shown in TABLE 2, the selection event for Click1 has a timestamp of 1000 ms and selection location of coordinate [25,456]. Referring to TABLE 1, the fixation event for Fixation3 has a timestamp of 995 and duration of 402. In this instance, since the timestamp 1000 ms of the selection event for "Click1" falls within the time frame of the recorded fixation event for "Fixation3", a conventional method (implemented for block 204, FIG. 2) would simply identify Fixation3 as corresponding to the selection event for "Click1" based solely on the correspondence of the time data. However, from TABLES 1 and 2 we see that the selection location [25,456] of Click1 is relatively far from the fixation location [723,233] of Fixation3. In fact, the selection location [25,456] of Click1 more closely corresponds to the fixation location [58,501] of Fixation1 or Fixation2, for example.

Figure 3:
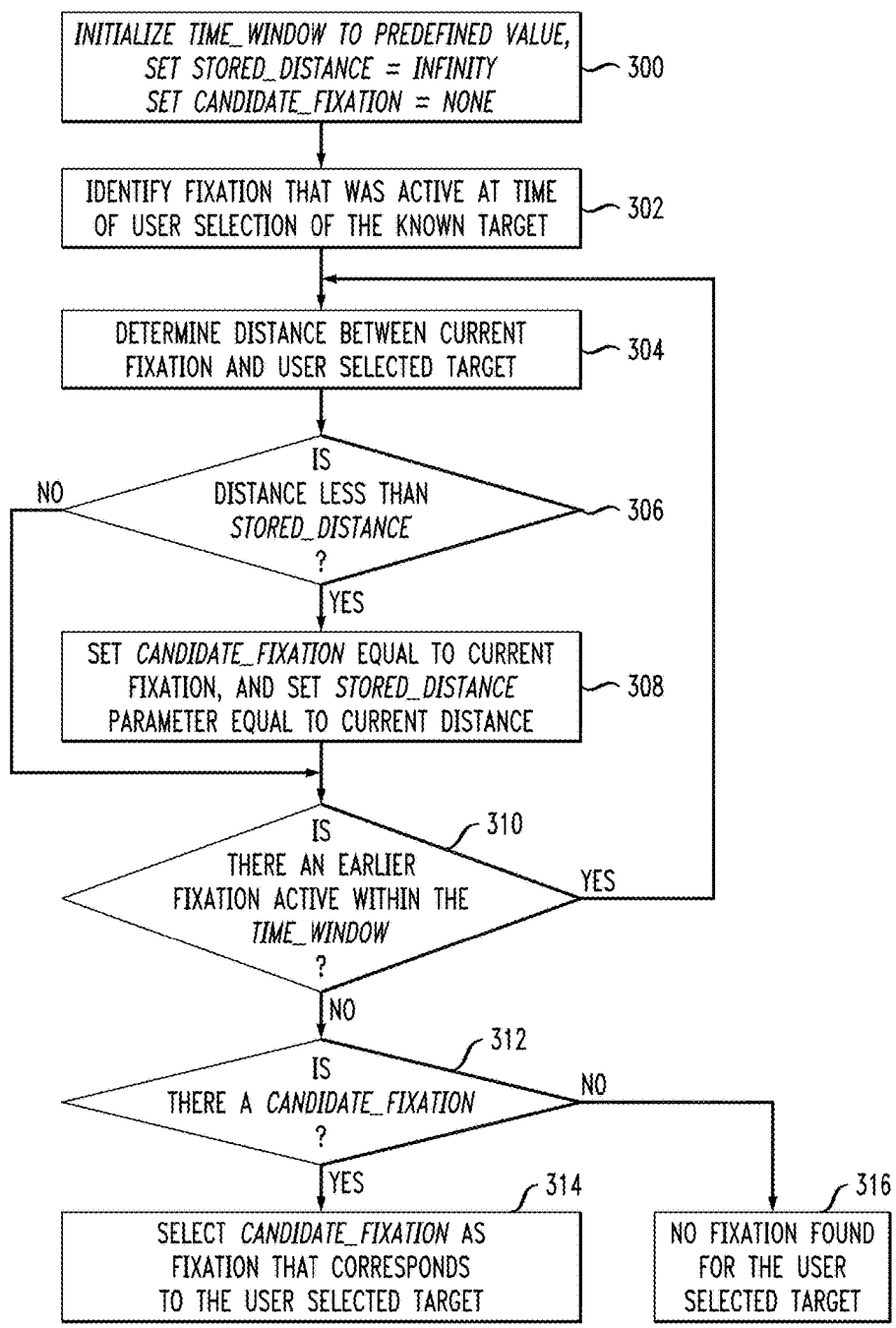
FIG. 3 is a flow diagram of a method which can be implemented in block 204 of FIG. 2 to identify a gaze point that corresponds to a user selected target, according to an embodiment of the invention.
Figure 4:
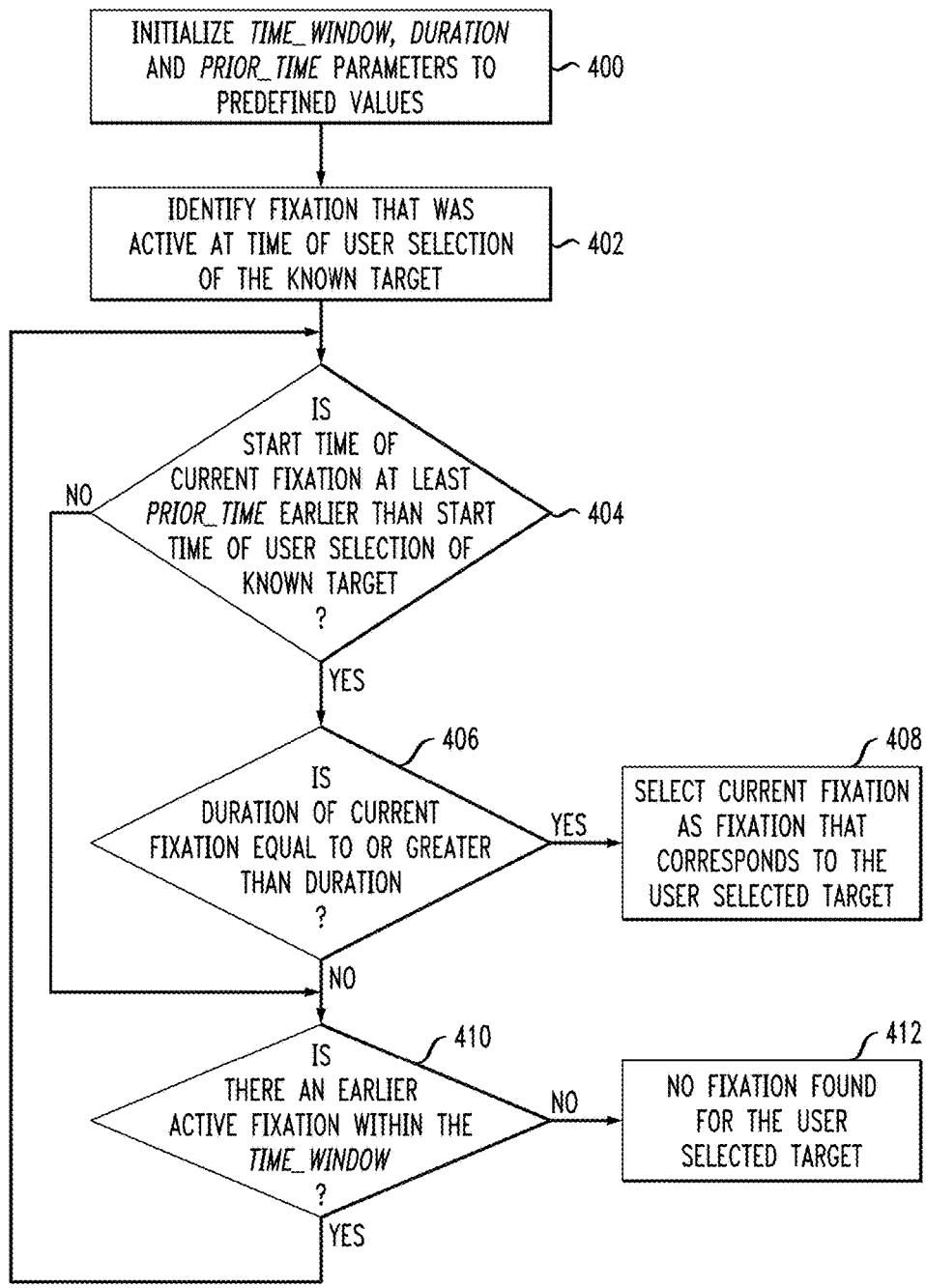
FIG. 4 is a flow diagram of a method which can be implemented in block 204 of FIG. 2 to identify a gaze point that corresponds to a user selected target, according to another embodiment of the invention.

In this regard, embodiments of the invention include methods for determining which fixation most likely corresponds to a given selection event for a known target. For example, FIGS. 3 and 4 illustrate methods according to alternate embodiments of the invention, which can be implemented in block 204 of FIG. 2 to identify a fixation that corresponds to a user selected target. In general, the method of FIG. 3 selects a given fixation which falls within a predefined time window (Time_Window) prior to the selection event, and which is nearest to a center region of the user selected target, as the fixation that is deemed most likely to be the fixation associated with the user selected target. In an alternative embodiment, the method of FIG. 4 selects a given fixation which falls within a predefined time window (Time_Window) prior to the selection event, and which is nearest in time to the selection event, and which has a minimum predefined duration (Duration) and a start time that is prior to the selection event by some predetermined amount of time (Prior_Time), as the fixation that is deemed most likely to be the fixation associated with the user selected target. The methods of FIGS. 3 and 4 will be explained in further detail below, and illustrated with the example data shown in TABLES 1, 2 and 3.

Referring to FIG. 3, an initial step includes initializing/setting various parameters to predetermined values (block 300). For example, in one embodiment of the invention, the parameters include Time_Window, Stored_Distance and Candidate_Fixation. The Time_Window parameter specifies a predefined window of time prior to the selection event (e.g., mouse click) wherein each active fixation within the time window is considered as a candidate fixation that may be associated with the selection event of the known target. In one embodiment of the invention, the Time_Window parameter is set to a predefined value of 500 ms. In one embodiment of the invention, the Stored_Distance parameter is initially set to "infinity" and updated during the process, as explained below. The Candidate_Fixation value is initially set to "none", and then updated during the process to include the index/label of a candidate fixation, as explained below.

A next step includes identifying which fixation, if any, was active at the time of the user selection of the known target (block 302). More specifically, in one embodiment of the invention, this step includes comparing the timestamp of the selection event for the known target in the selection event data file 152 with the timestamp and duration information of the fixation events in the fixation data file 150 to identify a fixation that was active at the time of the user selection of the known target. For example, using the example data shown in TABLE 2 above, we see that the selection event Click1 (which is associated with the user selected known target TargetA) has a timestamp of 1000 ms. Furthermore, based on the example data shown in TABLE 1, we see that Fixation3 was active at the time of selection event Click1 as the timestamp 1000 ms of Click 1 occurred during the time duration in which Fixation3 was active (i.e., Fixation3 specifies duration of 402 ms starting at time 995 ms and, therefore, has an end time of 1397 ms. It is to be noted that if no fixation is identified as being active at the time of the user selection of the known target (negative result in block 302), then the process flow proceeds to block 310 to determine if there is an earlier fixation active within the predefined Time_Window to be considered as a candidate fixation.

After identifying a fixation that was active at the time of the user selection of the known target, the process continues by determining a distance between the current fixation and the user selected target (block 304). More specifically, in one embodiment of the invention, the distance measure is determined by calculating a distance from the fixation location to the center location of the user selected target. Based on the example data from TABLES 1 and 3, we see that the user selected target TargetA (which is associated with the selection Click1) has a center location of [43, 430] and that the current fixation (Fixation3) has a fixation location of [723, 233]. Using the distance formula:

$$D = \sqrt[2]{(x_2 - x_1)^2 + (y_2 - y_1)^2},$$

the distance between the two x,y coordinates of [723, 233] and [43, 430] is 707.96.

A determination is then made as to whether the currently computed distance is less than the current value of Stored_Distance (block 306). If the currently computed distance is less than the value of Stored_Distance (affirmative determination in block 306), then the parameter Candidate_Fixation is set equal to the index of the current fixation, and the value of Stored_Distance is set equal to the currently computed distance (block 308). In the example process flow, the currently computed distance of 707.96 is less than the initial "infinity" value of Stored_Distance and, consequently, the value of Candidate_Fixation is updated from "none" to Fixation3, and the value of Stored_Distance is updated from "infinity" to a value of 707.97.

Next, a determination is made as to whether there is an earlier fixation event that was active within the predefined Time_Window (block 310). More specifically, in one embodiment of the invention, this determination in block 310 is made by referring to the fixation data file 150 to identify the next earliest fixation, which was recorded just prior to the currently considered fixation and which was active, in full or in part, during the predetermined Time_Window prior to the start time (timestamp) of the selection event. For example, assuming that Time_Window is 500 ms, referring to TABLE 1, we see that Fixation2 is the next earliest fixation event just prior to Fixation3, and that the fixation event Fixation2 was active in the 500 ms time window prior to the start time 1000 ms of the selection event Click1 (TABLE 2).

If it is determined that there is an earlier active fixation within the predefined Time_Window (affirmative determination in block 310), then that earlier active fixation becomes the current fixation under consideration, and the process flow continues (returns to block 304) to determine the distance between the current fixation and the user selected target. Continuing by way of example with reference to the data from TABLES 1 and 3, we see that the user selected target TargetA (which is associated with the selection Click1) has a center location of [43, 430], and that the current fixation (Fixation2) has a fixation location of [100, 512]. Using the distance formula $$D = \sqrt[2]{(x_2 - x_1)^2 + (y_2 - y_1)^2},$$

the distance between the two x,y coordinates of [100, 512] and [43, 430] is 99.86. Moreover, since the computed distance 99.86 for Fixation2 is less than the current Stored_Distance value of 707.97 for Fixation1 (affirmative determination in block 306), the value of Candidate_Fixation is updated from Fixation3 to Fixation2, and the value of Stored_Distance is updated from 707.97 to 99.86 (block 308).

Next, continuing with the process flow to block 310, and referring again to TABLE 1, we see that Fixation1 is the next earliest fixation event just prior to Fixation2, and that Fixation1 was active in the 500 ms time window prior to the start time 1000 ms of the selection event Click1 (TABLE 2) (affirmative determination in block 310). In this instance, Fixation1 becomes the current fixation under consideration, and the process flow continues (returns to block 304) to determine the distance between the current fixation and the user selected target. Continuing again by way of example with reference to the data from TABLES 1 and 3, we see that the user selected target TargetA (which is associated with the selection Click1) has a center location of [43, 430] and that the current fixation (Fixation1) has a fixation location of [58, 501]. Using the above distance formula, D, the distance between the two x,y coordinates of [58, 501] and [43, 430] is 72.57. Moreover, since the computed distance 72.57 for Fixation1 is less than the current Stored_Distance value of 99.86 for Fixation2 (affirmative determination in block 306), the value of Candidate_Fixation is updated from Fixation2 to Fixation1, and the value of Stored_Distance is updated from 99.86 to 72.57 (block 308).

Next, continuing with the process flow to block 310, and referring again to TABLE 1, we see that Fixation0 is the next earliest fixation event just prior to Fixation1, but that that Fixation0 was not active in the 500 ms time window prior to the start time 1000 ms of the selection event Click1 (TABLE 2) (negative determination in block 310). In this instance, the process flow proceeds to determine if there is a Candidate_Fixation (block 312). If there is a value for Candidate_Fixation other than the initial "none" value (affirmative determination in block 312), then the Candidate_Fixation is selected as the fixation that corresponds to the user selected target (block 314). For example, continuing with the above example, since the Candidate_Fixation parameter was set to Fixation1 at the time that it was determined (in block 310) that there were no more earlier active fixations within the predefined Time_Window, then Fixation1 is selected as the fixation that is associated with the selection Click1 of the user selected known target TargetA.

In circumstances where it is determined that there is no Candidate_Fixation (negative determination in block 312), then it will be deemed that no fixation corresponds to the selection event for the user selected target (block 316). For example, a Candidate_Fixation will not be found when, for example, there are one or more fixations that were identified as being active at the time of the selection event or within the Time_Window prior to the timestamp of the selection event, but where none of the computed distances between the user selected target and the one or more fixations fell below the initial threshold distance. Moreover, a Candidate_Fixation will not be found when, for example, there are no fixations identified as being active at the time of the selection event and when there are no fixations within the Time_Window prior to the timestamp of the selection event.

FIG. 4 illustrates an alternative embodiment of a method for implementing block 204 of FIG. 2 to identify a fixation that corresponds to a user selected target. While the method of FIG. 3 selects a given fixation which is active within a predefined time window prior to the selection event and which is nearest to a center region of the user selected target, as the fixation that is deemed most likely to the fixation associated with the user selected target, the method of FIG. 4 selects a given fixation which falls within a predefined time window (Time_Window) prior to the selection event, which is nearest in time to the selection event, and which has minimum predefined duration (Duration) and a start time that is prior to the selection event by some predetermined amount of time (Prior_Time), as the fixation that is deemed most likely to the fixation associated with the user selected target.

Referring to FIG. 4, an initial step includes initializing/setting various parameters to predefined values (block 400). For example, in one embodiment of the invention, the parameters include Time_Window, Duration and Prior_Time. As with the method of FIG. 3, the Time_Window parameter specifies a predefined window of time prior to the start time of a given selection event (e.g., mouse click) in which active fixations within the time window are considered as a candidate fixation that may be associated with the selection event of the known target. In one embodiment of the invention, the Time_Window parameter is set to a predefined value of 500 ms. The Duration parameter specifies a minimum amount of time that a given fixation must be active to be considered as a candidate fixation that may be associated with the selection event of the known target. In one embodiment, the Duration parameter is set to a predefined value of 100 ms. The Prior_Time parameter specifies a predefined window of time prior to the start time of a selection event. In one embodiment of the invention, the Prior_Time is set to a predefined value of 300 ms.

A next step includes identifying which fixation, if any, was active at the time of the user selection of the known target (block 402). More specifically, in one embodiment of the invention, this step includes comparing the timestamp of the selection event for the known target (as provided in the selection event data file 152) with the timestamp and duration information of the fixation events (as provided in the fixation data file 150) to identify a fixation that was active at the time of the user selection of the known target.

After identifying the fixation that was active at the time of the user selection of the known target, a determination is then made as to whether the start time of the currently identified fixation is at least Prior_Time earlier than the start time of the selection event of the known target (block 404). If so (affirmative determination in block 404), then a determination is made as to whether a duration of the current fixation is equal to or greater than the predefined Duration (block 406). If so (affirmative determination in block 406), then the current fixation is selected as the fixation that corresponds to the user selected target (block 408).

On the other hand, if no fixation is identified as being active at the time of the user selection of the known target (negative result in block 402), then the process flow proceeds to determine whether there is an earlier fixation event that was active within the predefined Time_Window (block 410). More specifically, in one embodiment of the invention, this determination in block 410 is made by referring to the fixation data file 150 to identify the next earliest fixation that was recorded during the predetermined Time_Window prior to the start time (timestamp) of the selection event. If there is no earlier fixation event that was active within the predefined Time_Window (negative determination in block 410), then it is determined that no fixation is found for the user selected target (block 412).

Moreover, if there is a fixation that is identified as being active at the time of the user selection of the known target (affirmative result in block 402), but either the start time of the identified fixation does not meet the Prior_Time condition set forth in block 404, or that the duration of the identified fixation does not meet the Duration condition set forth in block 406, then the process flow proceeds to determine whether there is an earlier fixation event that was active within the predefined Time_Window (block 410). If there is no earlier fixation event that was active within the predefined Time_Window (negative determination in block 410), then it is determined that no fixation is found for the user selected target (block 412).

On the other hand, if there is an earlier fixation event that was active within the predefined Time_Window (affirmative determination block 410), then that earlier fixation is selected as the current fixation to be considered as a candidate. Then, a determination is made as to whether the start time of the current fixation is at least Prior_Time earlier than the start time of the selection event of the known target (block 404), and whether a duration of the current fixation is equal to or greater than the predefined Duration (block 406). If both conditions are met (affirmative determination in blocks 404 and 406), then the current fixation is selected as the fixation that corresponds to the user selected target (block 408).

If one of the conditions is not met (negative determination in block 404 or block 406), then the process flow proceeds to determine whether there is another earlier fixation event that was active within the predefined Time_Window (block 410) just prior to the current fixation under consideration. This process flow (blocks 410, 404, 406) is repeated to identify a fixation, if any, that meets all conditions as specified in blocks 410, 404 and 406, in which case that condition will be selected as the fixation that corresponds to the user selected target (block 408).

For purposes of illustration, the process flow of FIG. 4 will discussed using the example data shown in TABLES 1, 2 and 3 above. For example, assume that we are trying to find a fixation (in TABLE 1) that corresponds to the selection event Click1 (in TABLE 2). From TABLE 2, we see that the selection event Click1 (which is associated with the user selected known target TargetA) has a timestamp of 1000 ms. Furthermore, based on the example data shown in TABLE 1, we determine (in block 402) that Fixation3 was active at the time of the selection event Click1 because the timestamp of 1000 ms for Click 1 occurred during the time period in which Fixation3 was active (i.e., Fixation3 starts at time 995 ms and has a duration of 402 ms, and thus ends at time 1397 ms).

Furthermore, assuming a predefined Prior_Time of 300 ms and a predefined Duration of 100 ms, it is determined (in block 404) that the start time (995 ms) of Fixation3 is not Prior_Time (300 ms) earlier than the start time (1000 ms) of the user selection (Click1) of the known target (TargetA). Moreover, while the duration (402 ms) of Fixation3 is greater than the predefined Duration (100 ms), Fixation3 is not considered a candidate (due to the negative determination in block 404), and the process flow proceeds to determine whether there is an earlier fixation event that was active within the predefined Time_Window (block 410).

From TABLE 1, it is determined (in block 410) that Fixation2 is the next earliest fixation that was recorded during the predetermined Time_Window (e.g., 500 ms) prior to the start time of the selection event Click1. Moreover, since Fixation2 has a start time of 600 ms and a duration of 395 ms, it is affirmatively determined (in block 404) that the start time (600 ms) of Fixation2 is Prior_Time (e.g. 300 ms) earlier than the start time (1000 ms) of the user selection (Click1) of the known target (TargetA). Moreover, it is affirmatively determined (in block 406) that the duration (395 ms) of Fixation2 is greater than the predefined Duration (e.g., 100 ms). Consequently, Fixation2 is selected (in block 408) as the fixation that corresponds to the user selected target (TargetA) of the selection event Click1.

As noted above, FIGS. 3 and 4 illustrate methods according to alternate embodiments of the invention, which can be implemented in block 204 of FIG. 2 to identify a fixation that most likely corresponds to a user selected target of a given selection event. With the method of FIG. 3, the data files 150 and 152 are processed to determine a recorded fixation (i) which falls within a predefined time window prior to the time that the identified known target item was selected by the user, and (ii) which is nearest to a center region of the identified known target item selected by the user, as a recorded fixation that is deemed most likely to correspond to the identified known target item selected by the user. With the method of FIG. 4, the data files 150 and 152 are processed to determine a recorded fixation (i) which falls within a predefined time window prior to the time of selection of the identified known target item, (ii) which has a start time that is nearest in time to the time of selection of the identified known target item, but which start time is prior to the time of selection of the identified known target item by a predetermined amount of time, and (iii) which has a duration that meets a minimum predefined duration value, as a recorded fixation that is deemed most likely to correspond to the identified known target item selected by the user.

Referring back to FIG. 2, for each user selection of a known target determined to have a corresponding fixation (in block 204), a method is implemented to determine a distance vector between the user selected target and the corresponding fixation (block 206). For example, in one embodiment of the invention, a distance vector is calculated between the fixation location (e.g., fixation location specified in TABLE 1, for example) and the center location of the associated known target (location information as shown in TABLE 3, for example).

The distance vector for each identified fixation/target pair is stored as calibration error information for the fixation/target pair (block 208). For example, in the system 100 of FIG. 1, this calibration error information is stored in the calibration error data store 146. It is to be understood that the error information will typically vary across different parts of the display screen. For example, in a center region of the screen, the systematic error may be relatively small as compared to the top, bottom, left and right sides of the screen where the systematic error between associated fixation/selection events may increase in regions of the display screen further from the center region of the screen, and be relatively large in the extreme left/right/top/bottom regions of the screen. However, it is to be appreciated that the calibration error information computed and stored in blocks 206 and 208 provides error information between associated fixation/selection events in different regions of the display screen.

Following the processing in block 204, there may exist fixation events that were not identified as being associated with any user selection of a known target. In this regard, another method is implemented (blocks 210-222) in FIG. 2 to process the remaining set of fixations that were not associated with a user selection of a known target. As noted above, the eye tracker data comprises a sequence of fixations that are captured and recorded as a user gazes at one or more displayed items on a display screen while performing a computer task. There can be long periods of time in which no user selection events (e.g., mouse clicks) occurred while the user was looking around a given screen to perform a task. In some instances, it is desirable to determine what displayed items a user was looking while performing a computer task. In this regard, the following method (blocks 210-222) provides a calibration error correction process for fixations that are not specifically associated with user selections of known targets, according to an embodiment of the invention.

An initial step is to identify the set of remaining fixations having no corresponding known target (block 210). For example, in one embodiment of the invention, this step can be performed by identifying each fixation event in the fixation data file 150 with a fixation that was not identified in block 204 as being associated with a user selection of a known target. Once the set of remaining fixations is identified (block 210), an iterative process is performed (blocks 212-220) to determine calibration error information for each fixation in the given set. The process comprises selecting a fixation in the set (block 212) and determining a candidate set of user selections of known targets which occurred with a predefined time window before and after the selected fixation (block 214). For example, assume that the selected fixation was recorded at time 10, we may look at the time period of 5-15 to identify all user selected known targets that were recorded in the time period of 5-15. With this step, we select as candidates only those user selected known targets within a given time window surrounding the selected fixation. In an alternate embodiment of the invention, the time window includes the entire duration of the recorded data.

Then, with the fixation location of the selected fixation being deemed the origin of a coordinate space surrounding the selected fixation, for each quadrant of space surrounding the selected fixation, we select (from the candidate set of user selection of known targets) the closest known target to the selected fixation (block 216). The location of a target used in calculating the distance between the target and a fixation is the average location of the fixations determined to be on that target. In one embodiment of the invention, fixations that are deemed "outliers" may be excluded from the computation of average fixation location (using a method as described below with reference to block 218). With this process, there will be at most one selected known target in each quadrant surrounding the selected fixation. Moreover, in some instances, a given quadrant will not contain any user selection of known targets in the candidate set and, therefore, no known target is selected for the given quadrant.

Next, for each selected known target in each quadrant, an average distance vector is determined between the selected known target and all fixations on the selected known target (block 218). In particular, in one embodiment of the invention, this process is performed by computing a distance vector between the center location of the selected known target and the fixation location of each fixation associated with that selected known target, and then taking an average of the distance vectors. This process takes into consideration that under certain circumstances, a user may have selected (clicked) on the same known target multiple times in the course of performing given task within the given time window used in block 214 to determine the candidate set of user selections of known targets. The process in block 218 is repeated for each quadrant.

Furthermore, in one embodiment of the invention, in block 218, fixations that are deemed "outliers" may be excluded from the average distance vector computation in block 218. For example, assume that for a given selected known target in a given quadrant, there are 6 fixations associated with that selected known target. Moreover, assume that 5 of these fixations have locations that are close to each other (e.g., within a range of 25-30 pixels below and to the right of the center coordinate of the selected known target, and that one of these fixations is located 150 pixels above and to the left of the center coordinate of the selected known target. In this example, the one fixation located 150 pixels above and to the left of the center coordinate of the selected known target fixation can be deemed an outlier and omitted from the average distance vector computation in block 218. The omission of the outlier(s) provides a more accurate reading on the error at the location of the selected known target.

A next step in the process includes using the average distance vectors (computed in block 218) to determine an error vector for the selected fixation using a weighted mean computation and storing the error information associated with the selected fixation (block 220). More specifically, in one embodiment of the invention, a weighted mean computation is performed by determining a mean of the average distance vectors computed in block 218, wherein the average distance vectors are weighted according to the distance between the selected fixation under consideration and the selected known targets associated with the distance vectors. For example, a higher weight is given to the average distance vector for a selected known target in a given quadrant that is close to the selected fixation, whereas lower weights are given to the average distance vectors for selected known targets in the other quadrants. In this process, we take a weighted average of the error in the x dimension and in the y dimension to compute the error vector for the selected fixation.

After the error vector for the selected fixation under consideration is determined and stored (in block 220), a next step includes determining if all fixations in the set of fixations have been processed (block 222). If there are remaining fixations in the set (negative determination in block 222), then the process proceeds to block 212 to select another fixation in the set, and blocks 214-220 are performed to compute an error vector for the newly selected fixation under consideration. Once all of the fixations in the set have been processed (affirmative determination in block 222), the calibration error computation process is completed.

At the conclusion of the calibration error computation process, the system has a stored set of error vectors for (i) fixations that are associated a user selection of known targets and (ii) fixations that are arbitrary and not associated with user selections of known targets. Indeed, as discussed above with reference to blocks 202-208, the error information computed for each fixation that is determined to be associated with a user selection of a known target is computed by determining a distance vector between the location of the fixation and the center of the user selected target. Moreover, as discussed above with reference to blocks 210-220, the error information computed for each arbitrary fixation that is not associated with a user selection of a known target is computed by determining a weighted average of a set of target fixations that are closest in both space and time to the arbitrary fixation.

After the calibration error computation process is completed, the stored error information can be utilized for a calibration error correction process to correct the recorded locations of the fixations within the data set of the given user session (block 224). In particular, in one embodiment of the invention, a calibration error correction process can be implemented (via the fixation location correction module 148, FIG. 1) to correct fixation locations by subtracting the associated error vector from the recorded fixation location to obtain a corrected fixation location. In another embodiment of the invention, a calibration error correction process can be implemented in parallel with the calibration error computation process, whereby the location of a given fixation can be corrected once the error vector is computed for the given fixation.

To illustrate the efficacy of calibration error computation and correction methods discussed herein, we performed actual experiments in which eye tracking data was collected from a group of participants and processed using techniques as discussed herein. In our experiments, a group of participants performed a computer-based task while their eye movements were tracked. At regular intervals during the task, a calibration screen was presented, on which a set of calibration targets would appear, one at a time, in a fixed set of locations. The participants were asked to look at and click on the displayed targets. FIGS. 5, 6, 7 and 8 illustrate experimental results of certain participants.

Figure 5:
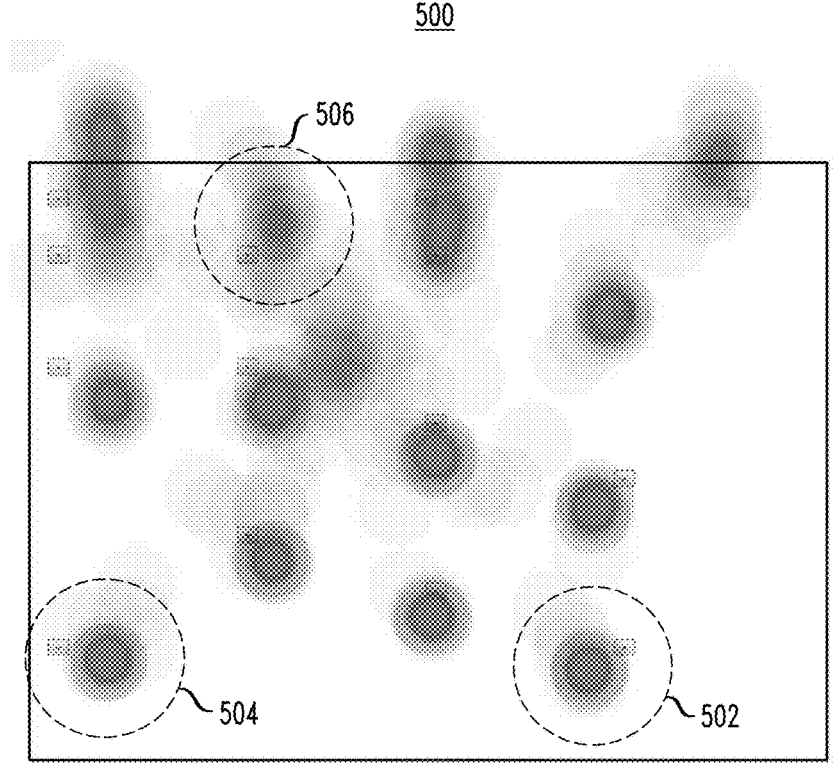
FIG. 5 illustrates an experimental set of eye tracking data having systematic calibration error.

For example, FIG. 5 illustrates an experimental set of eye tracking data having systematic calibration error, which was collected for a given participant. In particular, FIG. 5 depicts a heat map 500 that shows a set of fixations of the given participant on a calibration screen that was displayed to the given participant. A set of known targets that were displayed to the given participant are shown in FIG. 5 as squares containing a '+' sign. The shaded circles in various regions of the heat map 500 represent fixations in those regions. The duration of each fixation is indicated by the grayscale coloring, wherein a darker grayscale shading denotes a longer duration of the fixation. The heat map 500 of FIG. 5 shows tight circles of fixation, indicating that the given participant consistently looked at the targets. However, as shown in FIG. 5, the recorded fixation locations do not coincide with the screen locations of the targets and, therefore, a systematic calibration error is present in the eye tracking data.

In particular, for purposes of discussion, FIG. 5 illustrates three highlighted regions 502, 504 and 506 denoted by dashed circles. In the region 502, we see that the center of the fixation is located below and to the left of the displayed target. The same is generally true for the systematic calibration error of other fixation/target pairs in the lower right region of the display. In the region 504, the center of the fixation is located below and to the right of the display target. Moreover, the same is generally true for the systematic calibration error of other fixation/target pairs in the lower left region of the display. In the region 506, we see that the center of the fixation is located above and to the right of the displayed target. The same is generally true for the systematic calibration error of other fixation/target pairs in the upper left region of the display. Other patterns of systematic error in different regions of the display are also evident from the heat map 500 of FIG. 5.

Figure 6:
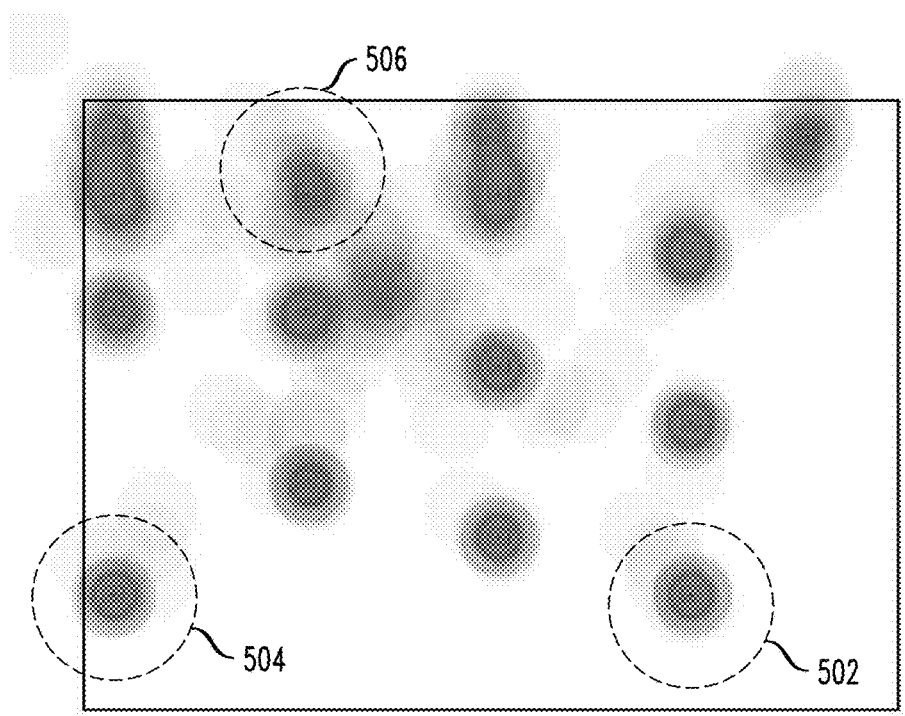
FIG. 6 illustrates the eye tracking data of FIG. 5 after correcting fixation locations of the captured eye tracking data using a systematic calibration error correction method, according to an embodiment of the invention.

FIG. 6 illustrates the eye tracking data of FIG. 5 after correcting fixation locations of the captured eye tracking data using a using systematic calibration error correction method, according to an embodiment of the invention. In particular, using techniques similar to those as discussed above with reference to FIG. 2, we computed error vectors for each fixation shown in FIG. 5 and used the error vectors to adjust the locations of fixations to coincide with corresponding displayed targets. Indeed, FIG. 6 is heat map 600 showing the corrected fixation locations. As compared to the fixation locations shown in FIG. 5, we see the result of fixation correction in FIG. 6 in which the fixation locations are shifted such that the center regions of the fixations are aligned to the corresponding displayed targets.

Figure 7:
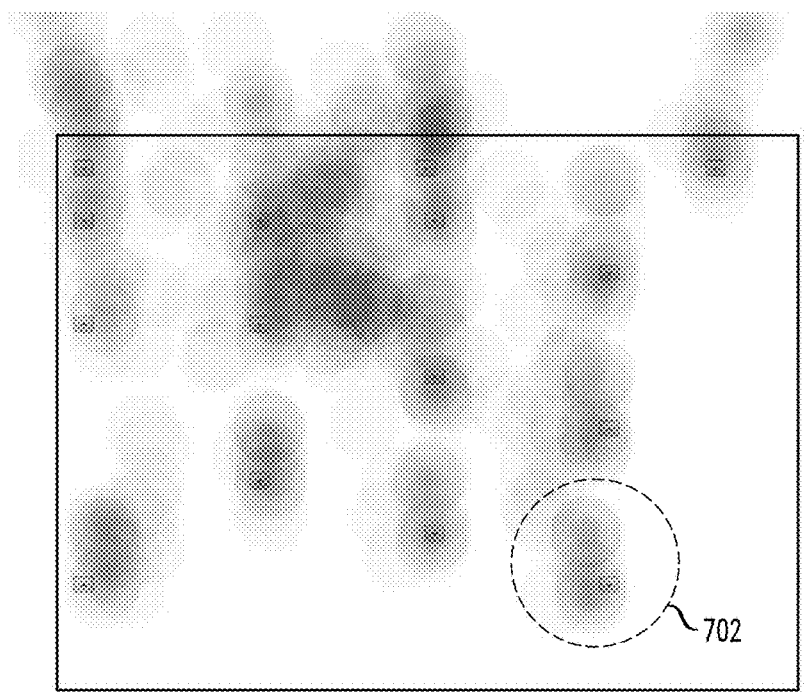
FIG. 7 illustrates another experimental set of eye tracking data having systematic calibration error.
Figure 8:
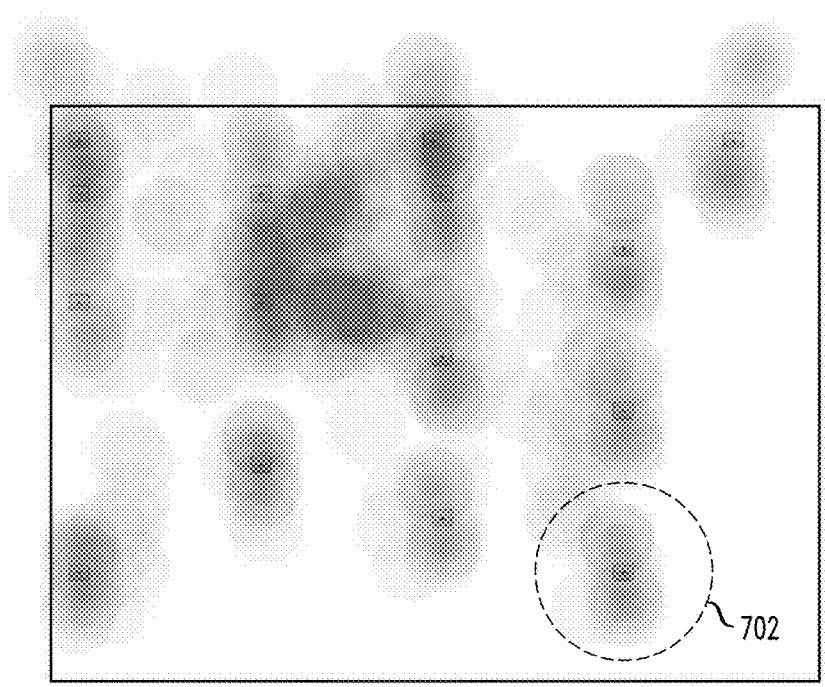
FIG. 8 illustrates the eye tracking data of FIG. 7 after correcting the systematic calibration error using a calibration error correction method that does not take into consideration shifts in calibration error patterns over time.
Figure 9:
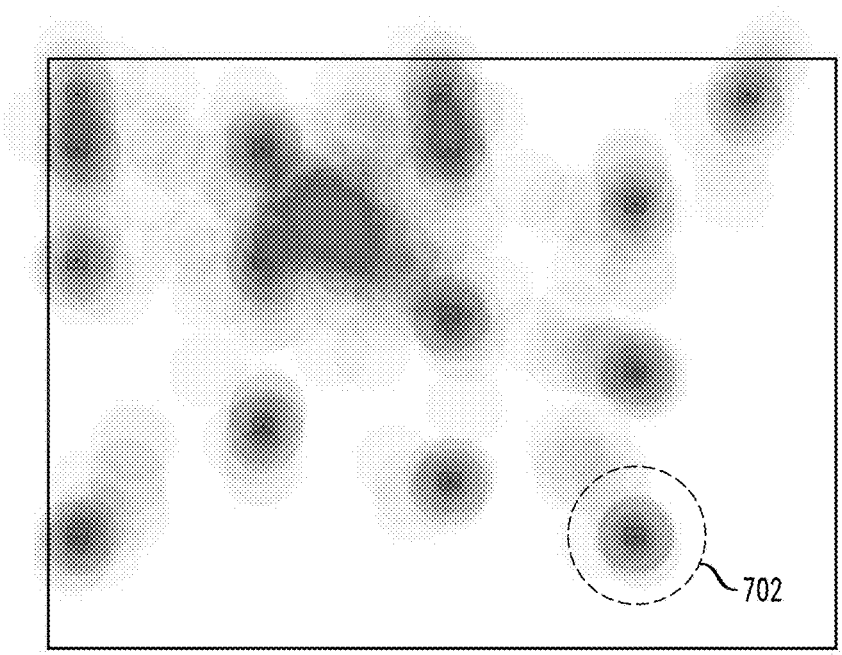
FIG. 9 illustrates the eye tracking data of FIG. 7 after correcting the systematic calibration error using a calibration error correction method that does take into consideration shifts in calibration error patterns over time, according to an embodiment of the invention.

In another embodiment of the invention, not specifically limited to eye gaze data, a systematic calibration error correction method accommodates shifts in error patterns over time. In particular, embodiments of the invention include a "local" method, which accommodates shifts in calibration error patterns over time caused by a change in position of the user. In one embodiment of the invention, a local method is realized by the use of a time window to determine a set of candidate user selections of known targets in a time window before and after a given fixation (e.g., block 214 in FIG. 2). This local approach could be applied to other kinds of data besides eye gaze data, in particular, any type of data that describes a location in 2 or 3 dimensions, for example. FIGS. 7, 8 and 9 illustrate these concepts of using a local method.

For example, FIG. 7 illustrates another experimental set of eye tracking data having systematic calibration error, which was collected for another participant. In particular, FIG. 7 depicts a heat map 700 that shows a set of fixations of the participant on a calibration screen that was displayed to the given participant on two separate occasions. A set of known targets that were displayed to the given participant are shown in FIG. 7 as squares containing a '+' sign. The shaded circles in various regions of the heat map 700 represent fixations in those regions. In the example shown in FIG. 7, the fixation areas are not tightly defined. In particular, for the certain targets (for example, region 702) there is a pattern of double circles, caused by a change in the participant's position during the experimental study.

FIG. 8 illustrates the eye tracking data of FIG. 7 after correcting the systematic calibration error using a "global" calibration error correction method that does not take into consideration shifts in calibration error patterns over time, whereas FIG. 9 illustrates the eye tracking data of FIG. 7 after correcting the systematic calibration error using a "local" calibration error correction method that does take into consideration shifts in calibration error patterns over time, according to an embodiment of the invention. With a global method applied to the raw data shown in FIG. 7, by comparing regions 702 in FIGS. 7 and 8, for example, we see from a heat map 800 in FIG. 8 that the fixation locations are located closer to their respective targets than in the raw data, but the double circles remain. For this particular data, the global correction method may actually move some fixation locations further from the target than they were originally. With a local method applied to the raw data shown in FIG. 7, by comparing regions 702 in FIGS. 7, 8 and 9, for example, we see from a heat map in 900 in FIG. 9 that the double circles of the fixations have been brought closer together, resulting in a better overall calibration.

It is to be appreciated that systematic calibration error computation and correction techniques as disclosed herein can utilized in various domains such as banking, retail, or any organization with a web presence. Eye tracking data is increasingly used to inform user interface design, and to provide a deeper understanding of responses to many kinds of visual information such as advertisements, web pages, and store displays. Methods of making post-hoc corrections for calibration problems are of value to any organization using eye tracking, allowing conclusions to be drawn even when the original calibration was problematic, or the participants shifted position.

In other embodiments of the invention, calibration methods as described herein can be utilized in real time to update correction values that are applied to a detected eye location in applications such as laptops and tablet devices that include built-in eye tracking capabilities. In such applications, a user moves his/her position relative to the tracker's sensor, systematic calibration errors are introduced. Embodiments of the invention can be utilized in such devices to provide correction so that the user doesn't have to recalibrate frequently, improving the performance of the eye tracking application.

In other embodiments of the invention, a local window approach to post-hoc error correction could be implemented for other types of sensor data that may be prone to drifting, or vulnerable to environmental effects that impact the calibration. For example, GPS location tracking and robot vision are applications in which a local approach can useful. By way of example, while driving a vehicle using a GPS, if the GPS readings over some portion of the journey do not match for a set of known locations, a calibration correction process as disclosed herein can be applied, using a time window of recent locations, and the measurements at those locations can be used to correct the full stream of GPS locations. Similarly, for robotic applications, a robot's perceived location based on computer vision may be affected by changes in the camera's position or angle. A calibration correction process according to an embodiment of the invention could be applied to recalibrate based on visiting known locations that are confirmed through other sensing methods.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

These concepts are illustrated with reference to FIG. 10, which shows a computing node 10 comprising a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

Figure 10:
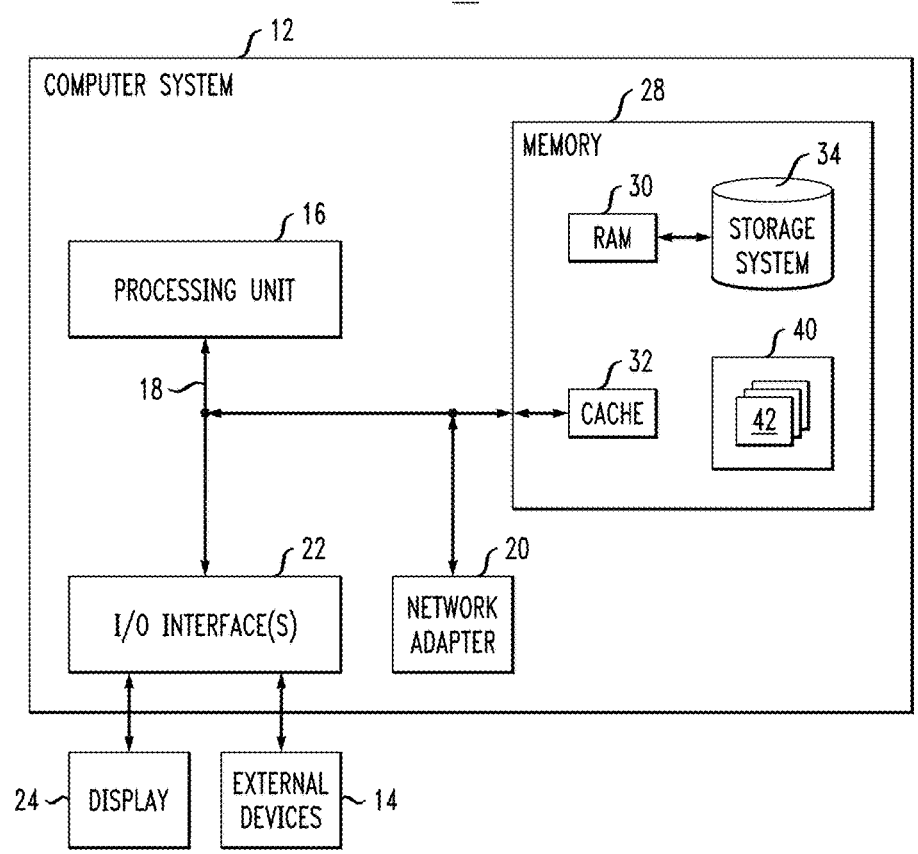
FIG. 10 illustrates a computer system that may be used to implement one or more components/steps of the techniques of the invention, according to an embodiment of the invention.

In FIG. 10, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

The bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 12 typically includes a variety of computer system readable media. Such media may be any available media that is accessible by computer system/server 12, and it includes both volatile and non-volatile media, removable and non-removable media.

The system memory 28 can include computer system readable media in the form of volatile memory, such as random access memory (RAM) 30 and/or cache memory 32. The computer system/server 12 may further include other removable/non-removable, volatile/nonvolatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As depicted and described herein, memory 28 may include at least one program product having a set (e.g., at least one) of program modules that are configured to carry out the functions of embodiments of the invention.

The program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for correcting systematic error in calibration data of an eye tracking system, comprising:

accessing recorded information that is associated with a given session in which a user performs a computer task while selecting known target items that are displayed on a display screen during the session and while using an eye tracking system to record locations of user fixations on the display screen as the user views the display screen during the session, wherein the recorded information comprises (i) fixation data that include start time, display screen location, and duration information for each of a plurality of fixations recorded during the session, (ii) selection event data that include start time and display screen location information for each of a plurality of user selection events recorded during the session; and (iii) known target location data that include display screen location information for each of a plurality of known target items that are displayed during the session;

processing the obtained information to identify a known target item selected by the user;

processing the obtained information to identify a recorded fixation, if any, which most likely corresponds to the identified known target item selected by the user, wherein a recorded fixation which was not active at a time that the identified known target item was selected by the user, is considered during said processing as a candidate fixation;

computing a distance vector between the identified recorded fixation and the corresponding identified known target item; and storing, in a data store, the computed distance vector as calibration error information for the identified recorded fixation and the corresponding identified known target item, wherein the accessing, processing, computing and storing are automated steps implemented by a computing device executing program code.

2. The method of claim 1, wherein processing the obtained information to identify a recorded fixation, if any, which most likely corresponds to the identified known target item selected by the user comprises determining a recorded fixation (i) which falls within a predefined time window prior to the time that the identified known target item was selected by the user, and (ii) which is nearest to a center region of the identified known target item selected by the user.

3. The method of claim 1, wherein processing the obtained information to identify a recorded fixation, if any, which most likely corresponds to the identified known target item selected by the user comprises determining a recorded fixation (i) which falls within a predefined time window prior to the time of selection of the identified known target item, (ii) which has a start time that is nearest in time to the time of selection of the identified known target item, but which start time is prior to the time of selection of the identified known target item by a predetermined amount of time, and (iii) which has a duration that meets a minimum predefined duration value.

4. The method of claim 1, further comprising:

processing the obtained information to identify a recorded fixation that does not correspond to a known target item selected by the user;

computing a calibration error vector for the identified fixation by taking a weighted average of distance measures of a set of target fixations that are nearest in both space and time to the identified fixation; and storing, in the data store, the computed calibration error vector as calibration error information for the identified fixation.

5. The method of claim 4, further comprising using the stored calibration error information to correct the fixation locations of the recorded fixations.

6. The method of claim 4, wherein computing a calibration error vector for the identified fixation, comprises:

processing the obtained information to determine a candidate set of user selections of known target items which occurred with a predefined time window before and after a start time of the identified fixation;

setting a fixation location of the identified fixation as an origin of a coordinate space surrounding the identified fixation;

for each quadrant of the coordinate space surrounding the identified fixation, determining from the candidate set of user selections of known target items a closest known target to the identified fixation;

for each determined known target item in each quadrant, computing an average distance vector between the determined known target item and all recorded fixations on the determined known target item;

applying a weight to each of the computed average distance vectors, wherein the average distance vectors are weighted according to the distance between the identified fixation and the selected known targets associated with the distance vectors; and computing weighted mean of the weighted average distance vectors.

7. The method of claim 6, further comprising excluding a recorded fixation that is deemed an outlier from average distance vector computation step.

8. An article of manufacture comprising a computer readable storage medium having program code embodied therewith, wherein the program code is executable by a computer to cause the computer to perform an automated process to correct systematic error in calibration data of an eye tracking system, wherein the automated process comprises:

accessing recorded information that is associated with a given session in which a user performs a computer task while selecting known target items that are displayed on a display screen during the session and while using an eye tracking system to record locations of user fixations on the display screen as the user views the display screen during the session, wherein the recorded information comprises (i) fixation data that include start time, display screen location, and duration information for each of a plurality of fixations recorded during the session, (ii) selection event data that include start time and display screen location information for each of a plurality of user selection events recorded during the session; and (iii) known target location data that include display screen location information for each of a plurality of known target items that are displayed during the session;

processing the obtained information to identify a known target item selected by the user;

processing the obtained information to identify a recorded fixation, if any, which most likely corresponds to the identified known target item selected by the user, wherein a recorded fixation which was not active at a time that the identified known target item was selected by the user, is considered during said processing as a candidate fixation;

computing a distance vector between the identified recorded fixation and the corresponding identified known target item; and storing, in a data store, the computed distance vector as calibration error information for the identified recorded fixation and the corresponding identified known target item, wherein the accessing, processing, computing and storing are automated steps implemented by a computing device executing program code.

9. The article of manufacture of claim 8, wherein processing the obtained information to identify a recorded fixation, if any, which most likely corresponds to the identified known target item selected by the user comprises determining a recorded fixation (i) which falls within a predefined time window prior to the time that the identified known target item was selected by the user, and (ii) which is nearest to a center region of the identified known target item selected by the user.

10. The article of manufacture of claim 8, wherein processing the obtained information to identify a recorded fixation, if any, which most likely corresponds to the identified known target item selected by the user comprises determining a recorded fixation (i) which falls within a predefined time window prior to the time of selection of the identified known target item, (ii) which has a start time that is nearest in time to the time of selection of the identified known target item, but which start time is prior to the time of selection of the identified known target item by a predetermined amount of time, and (iii) which has a duration that meets a minimum predefined duration value.

11. The article of manufacture of claim 8, wherein the automated process further comprises:
processing the obtained information to identify a recorded fixation that does not correspond to a known target item selected by the user;
computing a calibration error vector for the identified fixation by taking a weighted average of distance measures of a set of target fixations that are nearest in both space and time to the identified fixation; and
storing, in the data store, the computed calibration error vector as calibration error information for the identified fixation.

12. The article of manufacture of claim 11, wherein the automated process further comprises using the stored calibration error information to correct the fixation locations of the recorded fixations.

13. The article of manufacture of claim 11, wherein computing a calibration error vector for the identified fixation, comprises:
processing the obtained information to determine a candidate set of user selections of known target items which occurred with a predefined time window before and after a start time of the identified fixation;
setting a fixation location of the identified fixation as an origin of a coordinate space surrounding the identified fixation;
for each quadrant of the coordinate space surrounding the identified fixation, determining from the candidate set of user selections of known target items a closest known target to the identified fixation;
for each determined known target item in each quadrant, computing an average distance vector between the determined known target item and all recorded fixations on the determined known target item;
applying a weight to each of the computed average distance vectors, wherein the average distance vectors are weighted according to the distance between the identified fixation and the selected known targets associated with the distance vectors; and
computing weighted mean of the weighted average distance vectors.

14. The article of manufacture of claim 13, wherein the automated process further comprises excluding a recorded fixation that is deemed an outlier from average distance vector computation step.

15. A system, comprising:
a display device having a display screen;
an eye tracker system configured to record locations of user fixations on the display screen as the user views the display screen during a session in which the user performs a computer task while selecting known target items that are displayed on the display screen;
a computing system comprising a memory configured to store program code, and a processor device configured to execute the program code stored in the memory to implement an automated process to correct systematic error in calibration data of the eye tracker system, wherein the automated process comprises:
accessing recorded information that is associated with the given session, wherein the recorded information comprises (i) fixation data that include start time, display screen location, and duration information for each of a plurality of fixations recorded during the session, (ii) selection event data that include start time and display screen location information for each of a plurality of user selection events recorded during the session; and (iii) known target location data that include display screen location information for each of a plurality of known target items that are displayed during the session;
processing the obtained information to identify a known target item selected by the user;
processing the obtained information to identify a recorded fixation, if any, which most likely corresponds to the identified known target item selected by the user, wherein a recorded fixation which was not active at a time that the identified known target item was selected by the user, is considered during said processing as a candidate fixation;
computing a distance vector between the identified recorded fixation and the corresponding identified known target item; and
storing, in a data store, the computed distance vector as calibration error information for the identified recorded fixation and the corresponding identified known target item,
wherein the accessing, processing, computing and storing are automated steps implemented by a computing device executing program code.

16. The system of claim 15, wherein processing the obtained information to identify a recorded fixation, if any, which most likely corresponds to the identified known target item selected by the user comprises determining a recorded fixation (i) which falls within a predefined time window prior to the time that the identified known target item was selected by the user, and (ii) which is nearest to a center region of the identified known target item selected by the user.

17. The system of claim 15, wherein processing the obtained information to identify a recorded fixation, if any, which most likely corresponds to the identified known target item selected by the user comprises determining a recorded fixation (i) which falls within a predefined time window prior to the time of selection of the identified known target item, (ii) which has a start time that is nearest in time to the time of selection of the identified known target item, but which start time is prior to the time of selection of the identified known target item by a predetermined amount of time, and (iii) which has a duration that meets a minimum predefined duration value.

18. The system of claim 15, wherein the automated process further comprises:
processing the obtained information to identify a recorded fixation that does not correspond to a known target item selected by the user;
computing a calibration error vector for the identified fixation by taking a weighted average of distance measures of a set of target fixations that are nearest in both space and time to the identified fixation; and
storing, in the data store, the computed calibration error vector as calibration error information for the identified fixation.

19. The system of claim 18, wherein the automated process further comprises using the stored calibration error information to correct the fixation locations of the recorded fixations.

20. The system of claim 15, wherein computing a calibration error vector for the identified fixation, comprises:

processing the obtained information to determine a candidate set of user selections of known target items which occurred with a predefined time window before and after a start time of the identified fixation;

setting a fixation location of the identified fixation as an origin of a coordinate space surrounding the identified fixation;

for each quadrant of the coordinate space surrounding the identified fixation, determining from the candidate set of user selections of known target items a closest known target to the identified fixation;

for each determined known target item in each quadrant, computing an average distance vector between the determined known target item and all recorded fixations on the determined known target item;

applying a weight to each of the computed average distance vectors, wherein the average distance vectors are weighted according to the distance between the identified fixation and the selected known targets associated with the distance vectors; and computing a weighted mean of the weighted average distance vectors.

* * * * *